(12) United States Patent
Pei (10) Patent No.: US 8,516,880 B2
(45) Date of Patent: Aug. 27, 2013

(54) GAS SENSING SYSTEM WITH QUARTZ CRYSTAL SUBSTRATE

(75) Inventor: Shao-Kai Pei, Tu-Cheng (TW)

(73) Assignee: Hon Hai Precision Industry Co., Ltd., New Taipei (TW)

( * ) Notice: Subject to any disclaimer, the term of this patent is extended or adjusted under 35 U.S.C. 154(b) by 663 days.

(21) Appl. No.: 12/730,248

(22) Filed: Mar. 24, 2010

(65) Prior Publication Data

US 2010/0270153 A1   Oct. 28, 2010

(30) Foreign Application Priority Data

Apr. 25, 2009  (CN) .......................... 2009 1 0301837

(51) Int. Cl.
*G01N 29/24* (2006.01)
*G01N 29/36* (2006.01)

(52) U.S. Cl.
USPC ........................................ 73/24.01; 73/24.06

(58) Field of Classification Search
USPC .............................................. 73/24.01, 24.06
See application file for complete search history.

(56) References Cited

U.S. PATENT DOCUMENTS

| | | | | |
|---|---|---|---|---|
| 4,596,697 A * | 6/1986 | Ballato | ........................... | 422/98 |
| 4,703,646 A * | 11/1987 | Muller et al. | ................ | 73/24.01 |
| 6,997,039 B2 * | 2/2006 | Rao et al. | ..................... | 73/24.06 |
| 7,053,403 B1 * | 5/2006 | Zhang et al. | ..................... | 257/43 |
| 7,438,759 B2 * | 10/2008 | Zhang et al. | ...................... | 117/4 |
| 2006/0086314 A1 * | 4/2006 | Zhang et al. | ..................... | 117/98 |
| 2008/0277746 A1 * | 11/2008 | Hsu et al. | ...................... | 257/414 |

OTHER PUBLICATIONS

Chen, R.S. et al., "Growth and Characterization of Iridium Dioxide Nanorods", Journal of Alloys and Compounds, vol. 383, (2004), pp. 273-276.*

Chao, T.W. et al., "Quartz Crystal Microbalance Sensor Based on Nanostructured IrO2", Sensors and Actuators B, vol. 122 (2007), pp. 95-100.*

* cited by examiner

*Primary Examiner* — Daniel Larkin
(74) *Attorney, Agent, or Firm* — Altis Law Group, Inc.

(57) ABSTRACT

An exemplary gas sensing system includes a gas sensing unit, a detecting unit, and a processing unit. The gas sensing unit includes a quartz crystal substrate, a first electrode layer, a second electrode layer, a first activating layer, and a sensor medium layer having adsorption ability and desorption ability to chemical gas. The detecting unit is electrically connected with the first electrode and the second electrode, and is configured for detecting a frequency change of the gas sensing unit before and after adsorbing the chemical gas. The processing unit is electrically connected with the detecting unit, and is configured for obtaining a mass change of the gas sensing unit according to the frequency change.

15 Claims, 8 Drawing Sheets

FIG. 8

GAS SENSING SYSTEM WITH QUARTZ CRYSTAL SUBSTRATE

BACKGROUND

1. Technical Field

The present disclosure relates to a chemical sensing system, and particularly to a chemical gas sensing system for measuring gas concentrations.

2. Description of Related Art

Gas sensors are widely used to detect various chemical gases. Generally, gas sensors have a porous structure, and are capable of adsorption of chemical gases. Then a change in properties occurs, e.g., electrical resistance, transistor properties and the like, and a concentration of the gas can be obtained accordingly.

However, to ensure the gas sensors can be used repeatedly, it is required that gas sensors should have good desorption ability. Moreover, such gas sensors are not precise and sensitive enough.

What is needed, therefore, is to provide a gas sensing system which can overcome the aforementioned problems.

BRIEF DESCRIPTION OF THE DRAWINGS

Many aspects of the present gas sensing system can be better understood with reference to the following drawings. The components in the drawings are not necessarily drawn to scale, the emphasis instead being placed upon clearly illustrating the principles of the present lens module. Moreover, in the drawings, all the views are schematic, and like reference numerals designate corresponding parts throughout the several views.

DETAILED DESCRIPTION

Reference will now be made to the drawings to describe in detail the referred embodiments of the gas sensing system.

Figure 1:
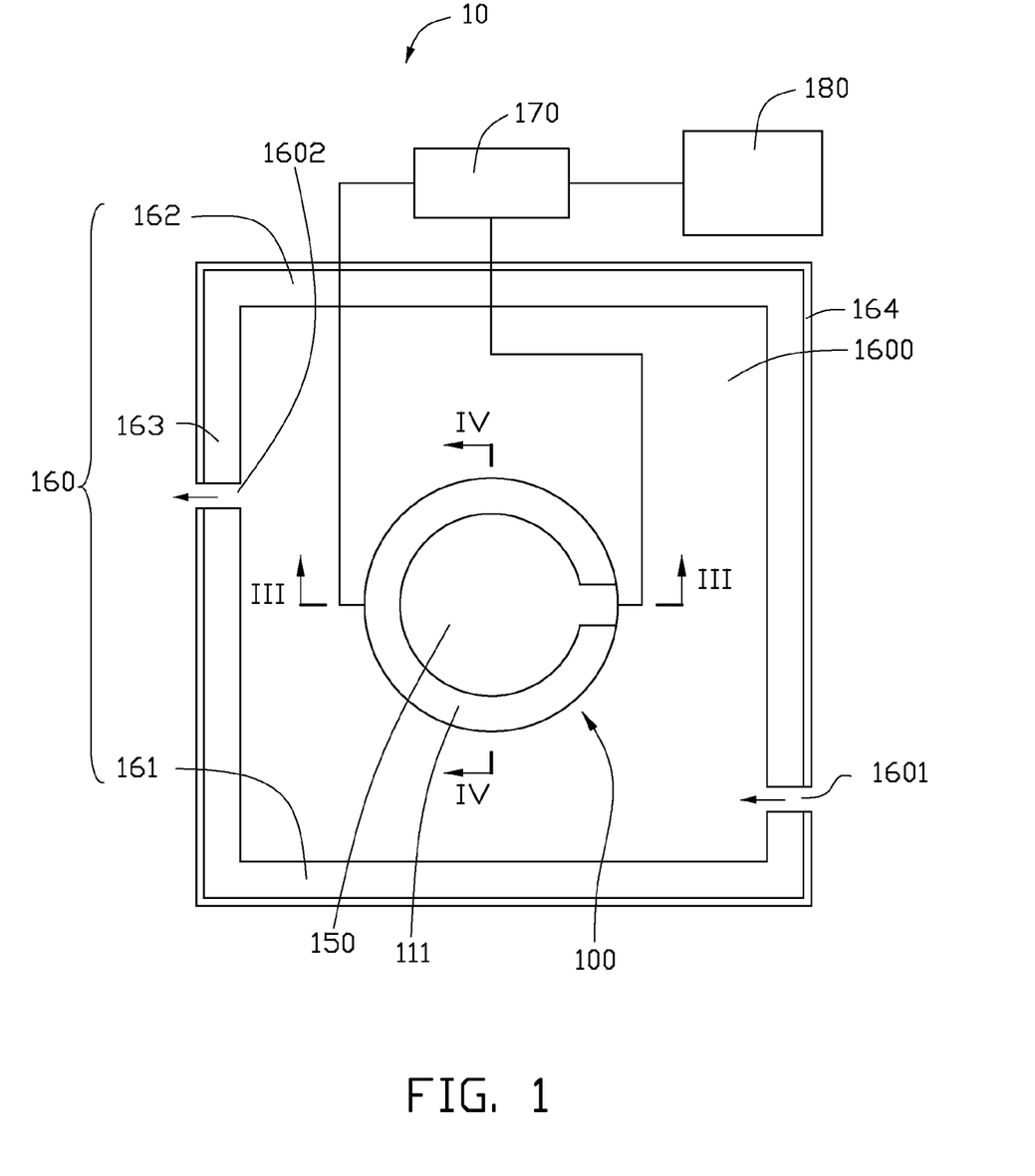
FIG. 1 is a schematic view of a gas sensing system in accordance with a first embodiment, including a front view of a gas sensing unit.
Figure 2:
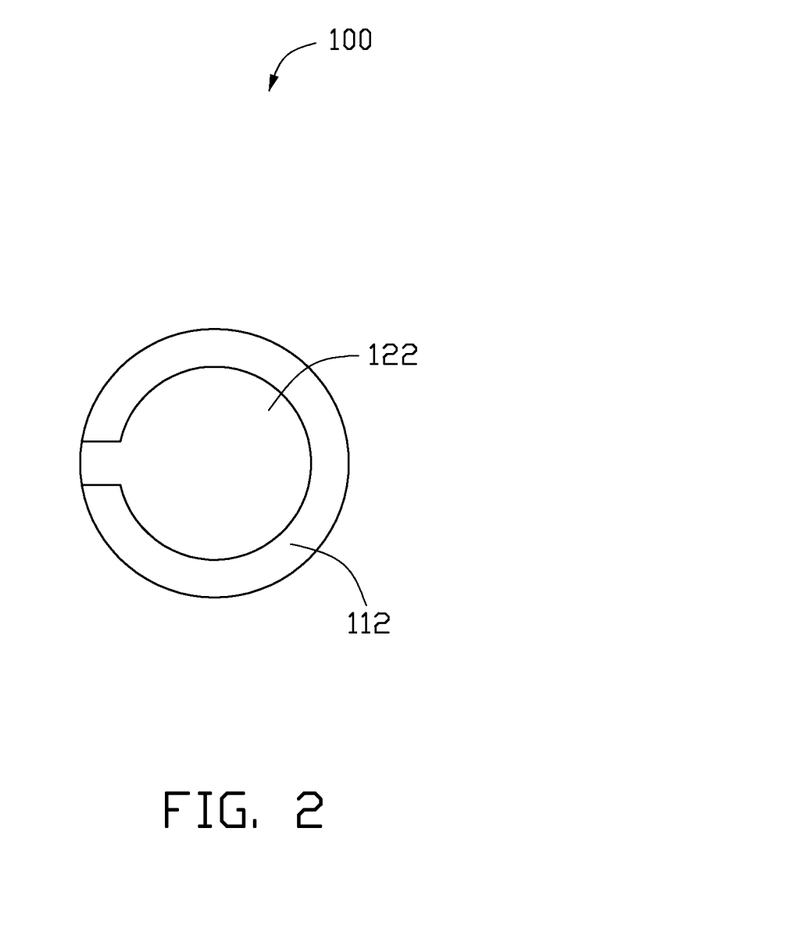
FIG. 2 is a rear view of the gas sensing unit of FIG. 1.

Referring to FIG. 1, a gas sensing system 10 includes a gas sensing unit 100, a chamber 160, a detecting unit 170, and a processing unit 180. The gas sensing unit 100 is configured for adsorbing chemical gas and desorbing a gas. The gas sensing unit 100 is arranged in the chamber 160, and is electrically connected to the detecting unit 170. The detecting unit 170 is configured for detecting the frequency change of the oscillation of the gas sensing unit 100, and transmitting the frequency change to the processing unit 180. The processing unit 180 is configured for obtaining a concentration of the chemical gas according to the frequency change.

In detail, referring to FIGS. 1 to 4, the gas sensing unit 100 includes a quartz crystal substrate 110, a first electrode layer 121, a second electrode layer 122, a first activating layer 130, a sensor medium layer 140, and a second activating layer 150. The quartz crystal substrate 110 has a circular cross section, and includes a first surface 111 and a second surface 112 at an opposite side thereof to the first surface 111. The first electrode layer 121 is formed on the first surface 111. The second electrode layer 122 is formed on the second surface 112. The first activating layer 130, the sensor medium layer 140, and the second activating layer 150 are formed on the first electrode layer 121 in sequence.

The quartz crystal substrate 110 has the reverse piezoelectric effect that it can mechanically deform in response to an applied electric field. Applying alternating electric fields to the quartz crystal substrate 110 will induce an oscillation with a resonant frequency equal to that of the alternating electric field. When the mass of the layers formed on the quartz crystal substrate 110 is changed, in other words, when the mass of the gas sensing unit 100 is changed, the frequency of the oscillation is changed accordingly. Under a predetermined condition with some assumptions, the frequency change can be quantified and correlated to the mass change using the Sauerbrey equation:

$$\Delta f = -\frac{2f_0^2}{A\sqrt{\rho_q \mu_q}} \Delta m$$

In the Sauerbrey equation, $f_0$ denotes the resonant frequency (Hz), $\Delta f$ denotes the frequency change (Hz), $\Delta m$ denotes the mass change (g), A denotes the piezoelectrically active crystal area (area of electrode, $cm^2$), $\rho_q$ denotes the density of quartz ($g/cm^3$), $\mu_q$ denotes the shear modulus of quartz ($g/cm.s^2$).

The first electrode layer 121 and the second electrode layer 122 can be gold, silver, or platinum layers, and can be formed on the quartz crystal substrate 110 by sputtering. In the illustrated embodiment, the first electrode layer 121 includes a first main portion 1211 formed on a central portion of the first surface 111 and a first connecting portion 1212 formed on a peripheral portion of the first surface 111. The first main portion 1211 has a substantially circular cross section, and the first connecting portion 1212 has a substantially rectangular cross section. The second electrode layer 122 includes a second main portion 1221 formed on a central portion of the second surface 112 and a second connecting portion 1222 formed on a peripheral portion of the second surface 112. The second main portion 1221 also has a substantially circular cross section, and a diameter of the second main portion 1221 is substantially equal to that of the first main portion 1211. That is, the orthographic projection of the second main portion 1221 coincides with that of the first main portion 1211. The second connecting portion 1222 also has a substantially rectangular cross section, and the orthographic projection of the first connecting portion 1212 and the orthographic projection of the second connecting portion 1222 are at two opposite sides of the orthographic projection of the second main portion 1221. The first connecting portion 1212 and the second connecting portion 1222 are electrically connected to the detecting unit 170, such that the detecting unit 170 can detect the frequency change of the gas sensing unit 100.

In the illustrated embodiment, the diameter of the second main portion 1221 is about 0.38 centimeters, a thickness of each of the first electrode layer 121 and the second electrode layer 122 is in the range from about 0.05 micrometers to 1 micrometer. In another embodiment, the thickness of each of the first electrode layer 121 and the second electrode layer 122 is in the range from approximately 0.1 micrometers to approximately 0.3 micrometers.

Figure 5:
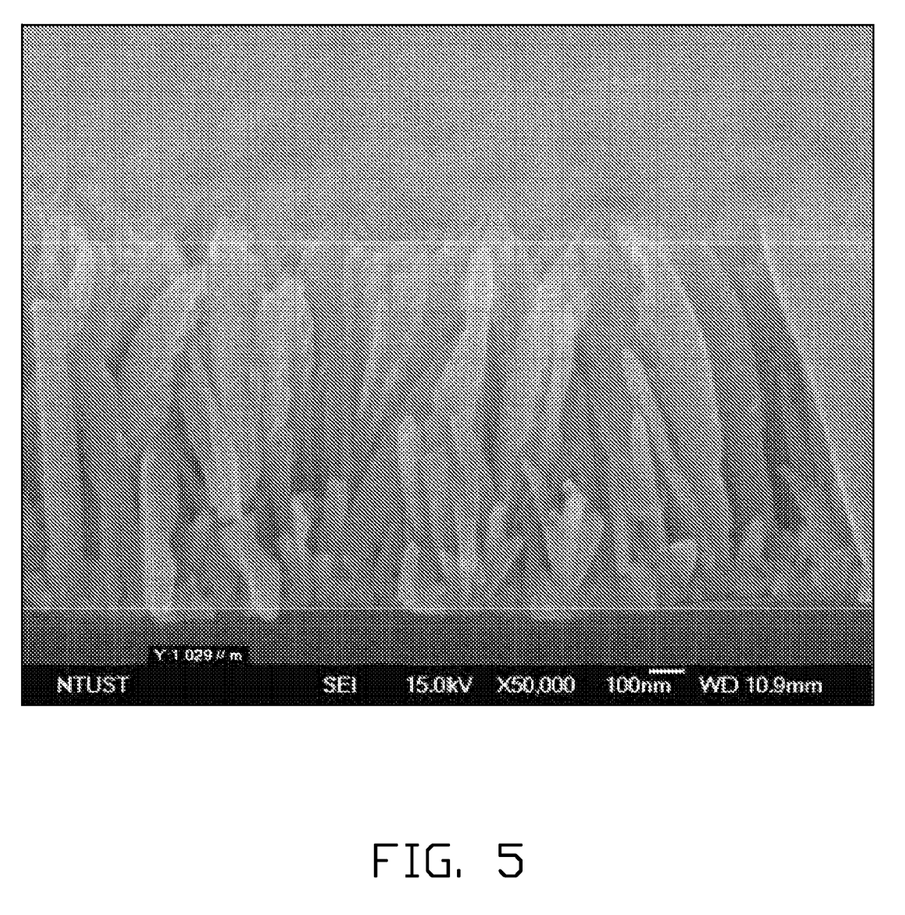
FIG. 5 is a scanning electron microscope (SEM) image of a cross-sectional view of part of the gas sensing unit of FIG. 1.
Figure 6:
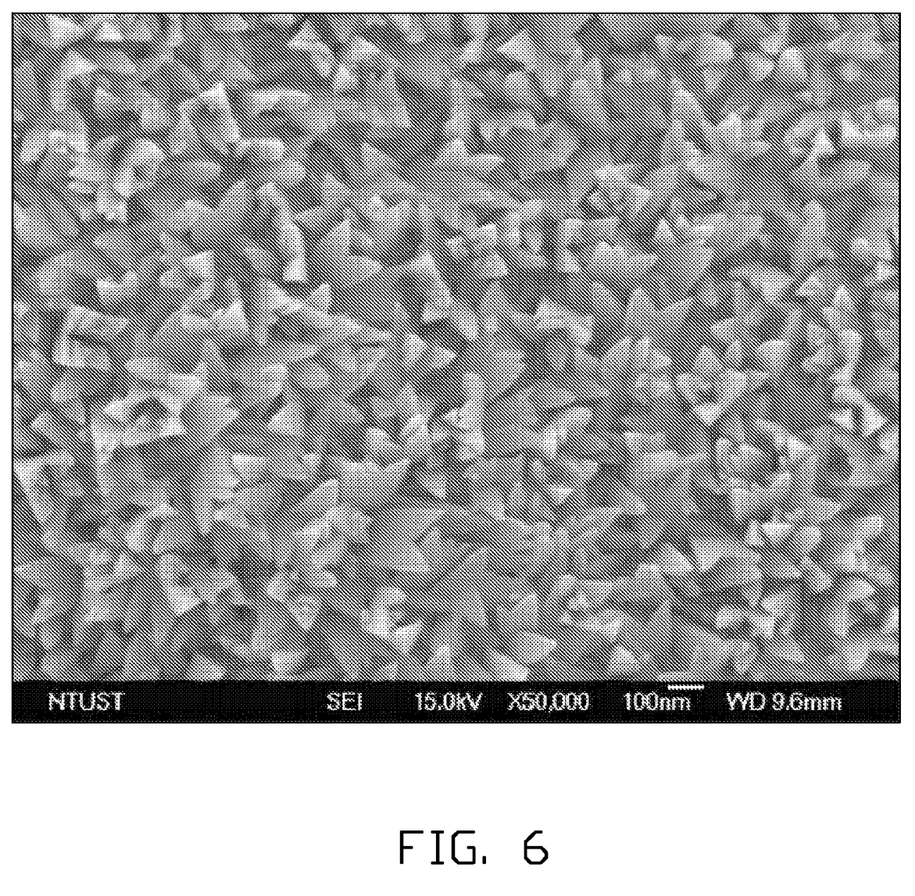
FIG. 6 is an SEM image of a front view of part of the gas sensing unit of FIG. 1.

The first activating layer 130 is in contact with the first electrode layer 121, the sensor medium layer 140 is arranged between and in contact with the first activating layer 130 and the second activating layer 150. The sensor medium layer 140 has a porous structure, and can adsorb as well as desorb amine gases and acidic gases. Specifically, the sensor medium layer 140 essentially consists of one-dimensional nanomaterial, which includes iridium dioxide ($IrO_2$) and iridium (Ir). The one-dimensional nanomaterial can be nanorods, nanotubes or composition of nanorods and nanotubes. In the illustrated embodiment, the sensor medium layer 140 consists of $IrO_2$ nanorods and Ir—$IrO_2$ nanorods. In another embodiment, referring to FIGS. 5 and 6, the sensor medium layer 140 can consist of $IrO_2$ nanotubes and Ir—$IrO_2$ nanotubes. In another embodiment, the sensor medium layer 140 can consist of $IrO_2$ nanorods, Ir—$IrO_2$ nanorods, $IrO_2$ nanotubes, and Ir—$IrO_2$ nanotubes. The Ir—$IrO_2$ nanorod is a nanorod with a composition that includes Ir and $IrO_2$. The Ir—$IrO_2$ nanotube is a nanotube with a composition that includes Ir and $IrO_2$. The sensor medium layer 140 is capable of adsorbing amine gas due to the fact that the $IrO_2$ nanorods and the Ir—$IrO_2$ nanorods can react with amine gas to form Ir—OH active functional groups. In addition, the sensor medium layer 140 is capable of adsorbing acidic gas due to the fact that the $IrO_2$ nanorods and the Ir—$IrO_2$ nanorods can react with acidic gas to form Ir—NH active functional groups. The sensor medium layer 140 has a thickness in the range from about 100 nanometers to 2 micrometers. In another embodiment, the thickness of the sensor medium layer 140 is in the range from 400 nanometers to 600 nanometers.

Figure 3:
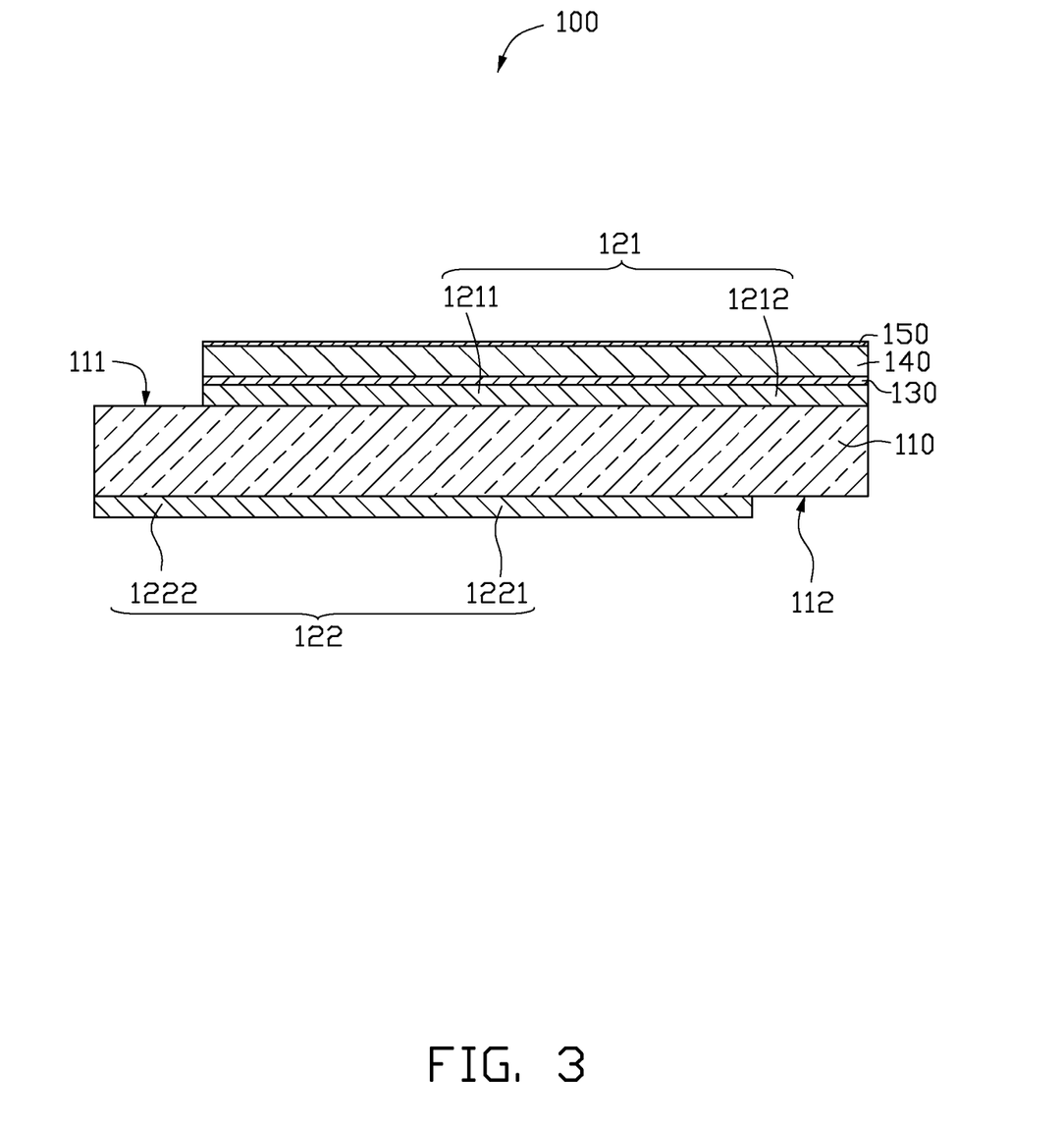
FIG. 3 is a cross-sectional sectional view of the gas sensing unit, taken along line III-III of FIG. 1.
Figure 4:
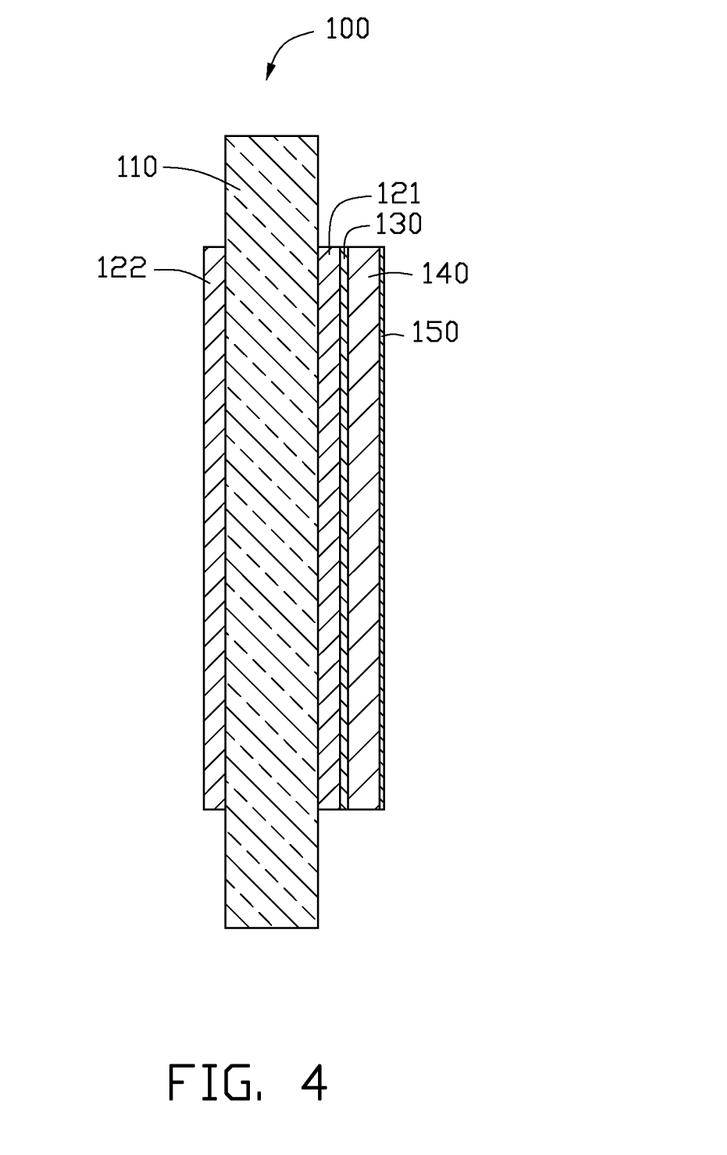
FIG. 4 is a cross-sectional sectional view of the gas sensing unit, taken along line IV-IV of FIG. 1.

In the illustrated embodiment, the sensor medium layer 140 can be formed on the first activating layer 130 in two steps, first, depositing $IrO_2$ nanorods on the first activating layer 130, second, deoxidizing the $IrO_2$ nanorods at high temperature to form $IrO_2$ nanorods and Ir—$IrO_2$ nanorods.

The first and second activating layers 130, 150 are at two opposite sides of the sensor medium layer 140, and are configured for activating the sensor medium layer 140. The first and second activating layers 130, 150 each essentially consist of cupric oxide, each can activate the sensor medium layer 140 because that cupric easily interacts with $IrO_2$ thereby forming lattice defects in the sensor medium layer 140 and then improving the adsorbing ability of the sensor medium layer 140. A thickness of each of the first activating layer 130 and the second activating layer 150 is in the range from 10 nanometers to 20 nanometers.

The chamber 160 is configured for receiving the gas sensing unit 100. The chamber 160 has a bottom wall 161, a top wall 162 opposite to the bottom wall 161, and an annulus side wall 163 connected between the bottom wall 161 and the top wall 162. The bottom wall 161, the top wall 162, and the side wall 163 define a receiving space 1600, in which the gas sensing unit 100 accommodated. An inlet 1601 and an outlet 1602 are defined in the side wall 163 at two opposite sides thereof. The inlet 1601 and the outlet 1602 are both in communication with the receiving space 1600, and are configured for introducing and exporting the chemical gas, respectively. In the illustrated embodiment, a thermal insulating cover 164 is disposed at the outside surface of the chamber 160, to maintain the temperature of the chemical gas introduced in the receiving space 1600.

The detecting unit 170 electronically communicates with the first electrode layer 121, the second electrode layer 122, and the processing unit 180. The detecting unit 170 is configured for detecting a frequency change of the gas sensing unit 100 before and after adsorbing the chemical gas, and transmitting the frequency change to the processing unit 180. The processing unit 180 is configured for obtaining a mass change of the gas sensing unit 100 before and after adsorbing the chemical gas according to the Sauerbrey equation.

The gas sensing system 10 can be used to precisely measure the concentration of amine gas and acidic gas. When amine gas or acidic gas is introduced into the receiving space 1600 of the chamber 160, the gas is adsorbed by the sensor medium layer 140 of the gas sensing unit 100, and then the mass of the gas sensing unit 100 is changed. Therefore, an oscillation frequency of the gas sensing unit 100 is changed. The detecting unit 170 can detect the frequency change, and the processing unit 180 can precisely calculate the mass change according to the Sauerbrey equation. In addition, the sensor medium layer 140 will desorb amine gas or acidic gas when nitrogen gas is introduced to the receiving space 1600. The gas sensing system 10 has high gas sensitivity and good desorption ability to amine and acidic gases.

Figure 7:
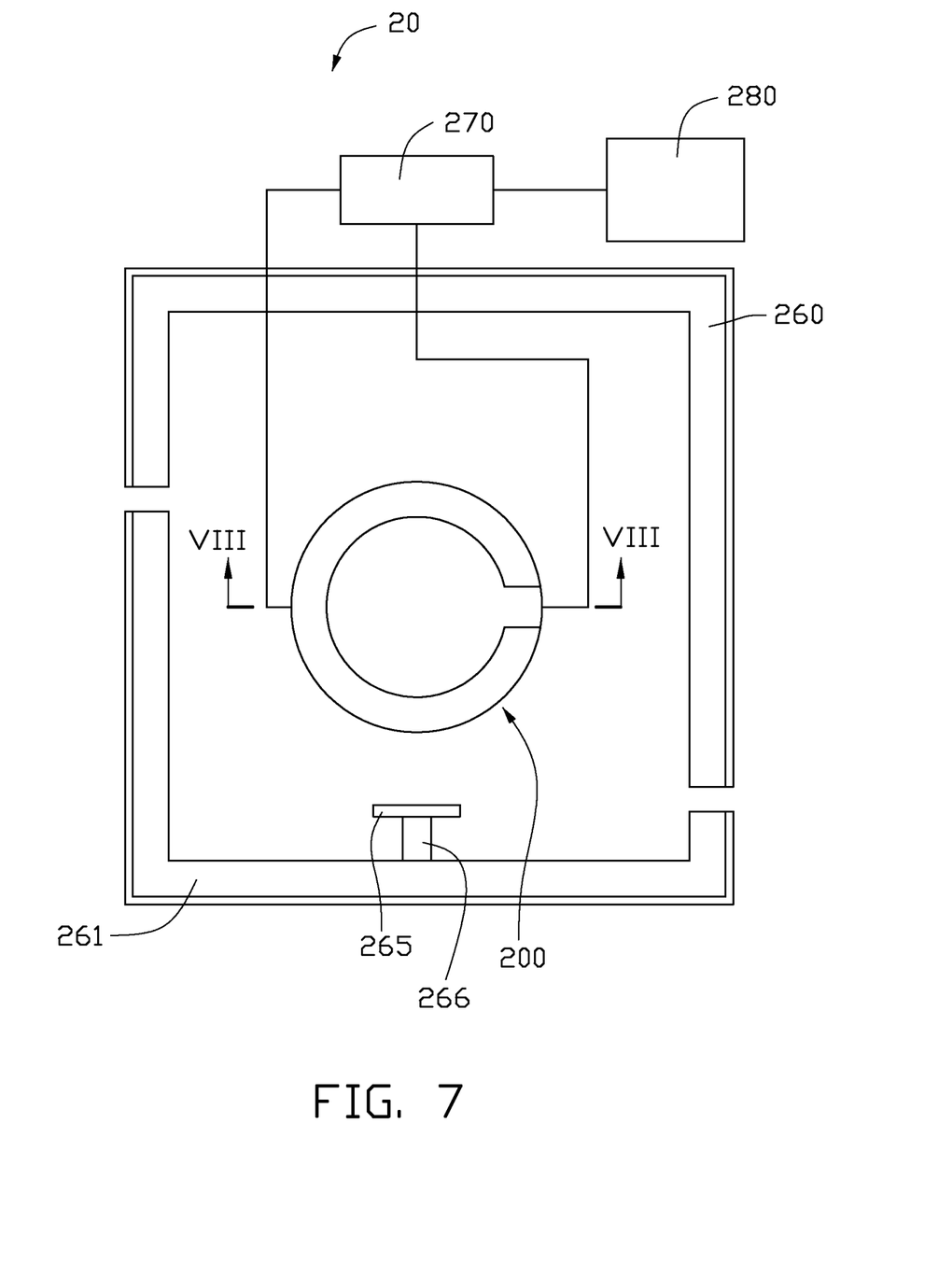
FIG. 7 is a schematic view of a gas sensing system in accordance with a second embodiment, including a front view of a gas sensing unit.

Referring to FIG. 7, a second embodiment of the gas sensing system 20 includes a gas sensing unit 200, a chamber 260, a detecting unit 270, and a processing unit 280. The gas sensing unit 200 has a structure and function similar to that of the gas sensing unit 100 of the first embodiment. The gas sensing unit 200 is arranged in the chamber 260, and is electrically connected to the detecting unit 270. The detecting unit 270 has a structure and function similar to that of the detecting unit 170 of the first embodiment, and is configured for detecting the frequency change of the oscillation of the gas sensing unit 200, and transmitting the frequency change to the processing unit 280. The processing unit 280 has a structure and function similar to that of the processing unit 180 of the first embodiment, and is configured for obtaining a concentration of the chemical gas according to the frequency change.

Figure 8:
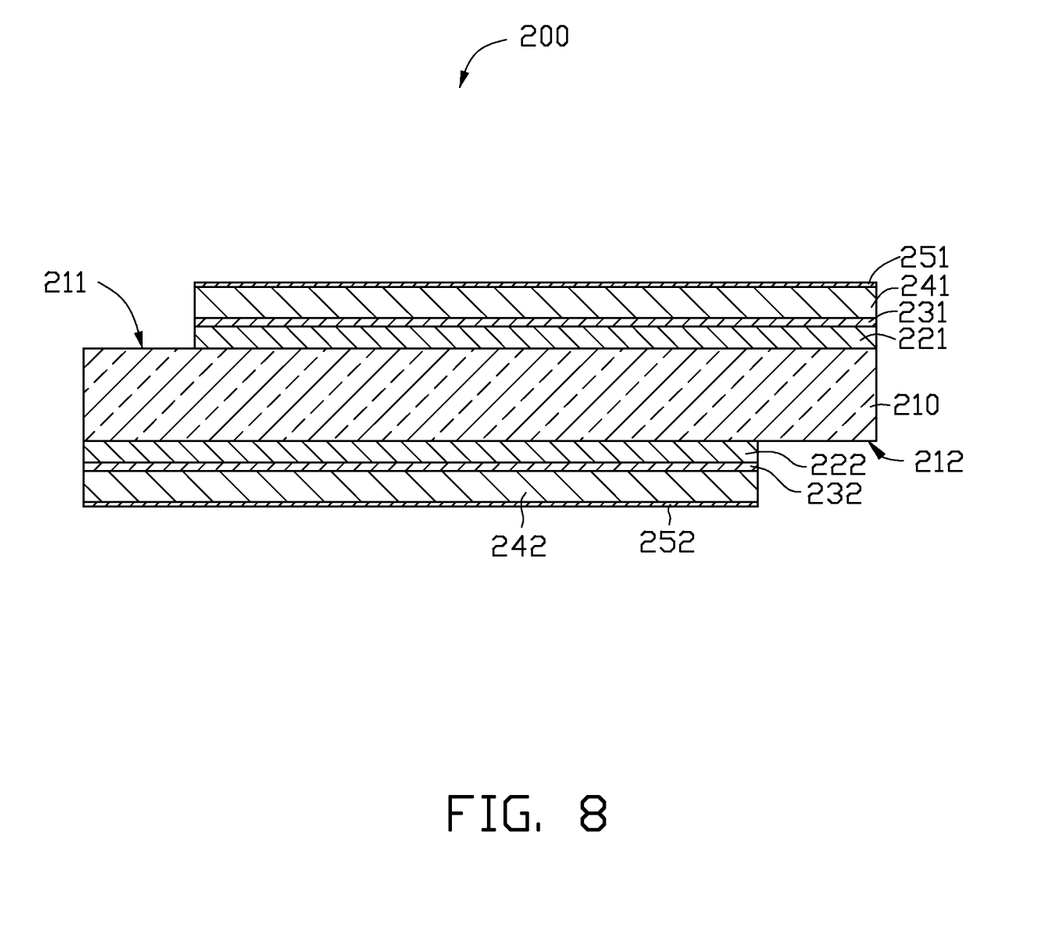
FIG. 8 is a cross-sectional schematic view of the gas sensing unit, taken along line VIII-VIII of FIG. 7.

Referring to FIG. 8, the gas sensing unit 200 has a quartz crystal substrate 210, a first electrode layer 221, a first activating layer 231, a first sensor medium layer 241, a second activating layer 251, a second electrode layer 222, a third activating layer 232, a second sensor medium layer 242, and a fourth activating layer 252. The quartz crystal substrate 210 has a first surface 211 and an opposite second surface 212. The first electrode layer 221, the first activating layer 231, the first sensor medium layer 241, and the second activating layer 251 are formed on the first surface 211 in sequence. The second electrode layer 222, the third activating layer 232, the second sensor medium layer 242, and the fourth activating layer 252 are formed on the second surface 212 in sequence. The first electrode layer 221 and the second electrode layer 222 are both electrically connected to the detecting unit 270. The first, second, third, and fourth activating layers 231, 251, 232, 252 are all cupric oxide layers, wherein the first and second activating layers 231, 251 are configured for activating the first sensor medium layer 241, the third and fourth activating layers 232, 252 are configured for activating the second sensor medium layer 242. The first and second sensor medium layers 241, 242 both consist of one-dimensional nanomaterial, which essentially consists of Ir and $IrO_2$.

The gas sensing unit 200 is received in a receiving space 2600 of the chamber 260. The chamber 260 includes a heating plate 265 accommodated in the receiving space 2600 under the gas sensing unit 200. Specifically, the heating plate 265 is fixed on a bottom wall 261 of the chamber 260, and is configured for heating chemical liquid flowed or dripped thereon into chemical gas.

In the illustrated embodiment, amine liquid or acidic liquid, which can be respectively vaporized to be amine gas or acidic gas, can be flowed or dipped onto the heating plate 265, and then a mass of the gas sensing unit 200 is changed. Therefore, an oscillation frequency of the gas sensing unit 200 is changed. The detecting unit 270 can detect the frequency change, and the processing unit 280 can calculate the mass change according to the Sauerbrey equation.

It is believed that the present embodiments and their advantages will be understood from the foregoing description, and it will be apparent that various changes may be made thereto without departing from the spirit and scope of the invention or sacrificing all of its material advantages, the examples hereinbefore described merely being preferred or exemplary embodiments of the invention.

The invention claimed is:

1. A gas sensing system, comprising:
a gas sensing unit, comprising:
a quartz crystal substrate comprising a first surface and a second surface at an opposite side thereof to the first surface;
a first electrode layer formed on the first surface;
a second electrode layer formed on the second surface;
a first activating layer formed on the first electrode layer, the first activating layer essentially consisting of cupric oxide; and
a first sensor medium layer formed on the first activating layer, the first sensor medium layer consisting of one-dimensional nanomaterial which comprises iridium dioxide and iridium, the first activating layer being configured for activating the first sensor medium layer, the first sensor medium layer being configured for adsorbing a chemical gas;
a detecting unit electrically coupled to the first electrode layer and the second electrode layer, the detecting unit being configured for detecting a frequency change of the gas sensing unit before and after adsorbing the chemical gas; and
a processing unit electrically connected to the detecting unit, the processing unit being configured for determining a mass change of the gas sensing unit before and after adsorbing the chemical gas according to the frequency change.

2. The gas sensing system of claim 1, wherein the gas sensing unit further comprises a second activating layer formed on the first sensor medium layer, the second activating layer essentially consists of cupric oxide.

3. The gas sensing system of claim 2, wherein a thickness of the second activating layer is in the range from 10 nanometers to 20 nanometers.

4. The gas sensing system of claim 1, wherein a thickness of the first activating layer is in the range from 10 nanometers to 20 nanometers.

5. The gas sensing system of claim 1, wherein the first electrode layer comprises a first main portion formed on a central portion of the first surface and a first connecting portion formed on a peripheral portion of the first surface, the second electrode layer comprises a second main portion formed on a central portion of the second surface and a second connecting portion formed on a peripheral portion of the second surface, an orthographic projection of the second main portion on the first electrode layer coincides with the first main portion, an orthographic projection of the first connecting portion on the second electrode layer and the second connecting portion are at two opposite sides of the second main portion.

6. The gas sensing system of claim 1, wherein the first electrode layer and the second electrode layer each essentially consist of a material selected from the group consisting of gold, silver, and platinum.

7. The gas sensing system of claim 6, wherein a thickness of each of the first electrode layer and the second electrode layer is in the range from 0.05 micrometers to 1 micrometer.

8. The gas sensing system of claim 6, wherein a thickness of each of the first electrode layer and the second electrode layer is in the range from 0.1 micrometers to 0.3 micrometers.

9. The gas sensing system of claim 1, wherein the first sensor medium layer essentially consists of $IrO_2$ nanorods and Ir—$IrO_2$ nanorods, each of the Ir—$IrO_2$ nanorods is a nanorod comprised of Ir and $IrO_2$.

10. The gas sensing system of claim 1, wherein the first sensor medium layer essentially consists of $IrO_2$ nanotubes and Ir—$IrO_2$ nanotubes, each of the Ir—$IrO_2$ nanotubes is a nanotube comprised of Ir and $IrO_2$.

11. The gas sensing system of claim 1, wherein the first sensor medium layer essentially consists of $IrO_2$ nanorods, Ir—$IrO_2$ nanorods, $IrO_2$ nanotubes, and Ir—$IrO_2$ nanotubes, each of the Ir—$IrO_2$ nanorods is a nanorod comprised of Ir and $IrO_2$, each of the Ir—$IrO_2$ nanorods is a nanotube comprised of Ir and $IrO_2$.

12. The gas sensing system of claim 1, wherein a thickness of the first sensor medium layer is in the range from 100 nanometers to 2 micrometers.

13. The gas sensing system of claim 1, wherein a thickness of the first sensor medium layer is in the range from 400 nanometers to 600 nanometers.

14. The gas sensing system of claim 1, further comprising a chamber configured for receiving the gas sensing unit.

15. The gas sensing system of claim 14, wherein the chamber defines a receiving space, an inlet, and an outlet, the gas sensing unit is accommodated in the receiving space, the inlet and outlet each are in communication with the receiving space, the inlet is configured for introducing the chemical gas, the outlet is configured for discharging the chemical gas.

* * * * *